(12) United States Patent
Tang et al.

(10) Patent No.: US 11,242,354 B2
(45) Date of Patent: Feb. 8, 2022

(54) 4-SULFUR SUBSTITUTED PODOPHYLLOTOXIN DERIVATIVE AND PREPARATION METHOD THEREFOR AND USE THEREOF

(71) Applicant: Yajie Tang, Hubei (CN)

(72) Inventors: Yajie Tang, Hubei (CN); Wei Zhao, Hubei (CN)

(73) Assignee: Yajie Tang

( * ) Notice: Subject to any disclaimer, the term of this patent is extended or adjusted under 35 U.S.C. 154(b) by 61 days.

(21) Appl. No.: 16/825,251

(22) Filed: Mar. 20, 2020

(65) Prior Publication Data

US 2020/0216462 A1    Jul. 9, 2020

Related U.S. Application Data

(63) Continuation of application No. PCT/CN2018/089832, filed on Jun. 4, 2018.

(30) Foreign Application Priority Data

Sep. 22, 2017 (CN) .......................... 201710912793.8

(51) Int. Cl.
  *C07D 493/04*   (2006.01)
  *A61P 35/00*    (2006.01)
  *C07D 471/04*   (2006.01)

(52) U.S. Cl.
  CPC ............ *C07D 493/04* (2013.01); *A61P 35/00* (2018.01); *C07D 471/04* (2013.01)

(58) Field of Classification Search
  CPC .............................. C07D 493/04; A61P 35/00
  See application file for complete search history.

(56) References Cited

U.S. PATENT DOCUMENTS

| 5,061,791 A | 10/1991 | Showalter et al. |
| 2016/0264592 A1 | 9/2016 | Tang et al. |

FOREIGN PATENT DOCUMENTS

| CN | 102757442 A | 10/2012 |
| CN | 102757443 A | 10/2012 |
| CN | 103613601 A | 3/2014 |
| CN | 108285456 A | 7/2018 |
| WO | 2004033423 A2 | 4/2004 |

OTHER PUBLICATIONS

STN Registry Entry for CAS RN 162898-27-3, Entry Date May 11, 1995, Accessed Jul. 15, 2021.*
International Search Report from Application No. PCT/CN2018/089823 dated Sep. 14, 2018, 3 pages.
Lu, Kuanke et al., "Synthesis of 4-S-(1"-Aryltetrazole-5"-Y1)-4-Deoxy-4'-Demethylepipodophyllotoxin Analogs", Chinese Chemical Letters, Mar. 30, 1995 (Mar. 30, 1995), pp. 197-198, vol. 6, No. 3.

* cited by examiner

*Primary Examiner* — Alicia L Otton
(74) *Attorney, Agent, or Firm* — Lerner, David, Littenberg, Krumholz & Mentlik, LLP

(57) ABSTRACT

Disclosed are a 4-sulfur substituted podophyllotoxin derivative and a synthetic method therefor and the use thereof. In the present invention, introducing heteroaromatic compounds with rigidity, such as 4-trifluoromethylpyridin-2-thiol, 4-trifluoromethyl-2-mercaptopyrimidine, and para-fluorothiophenol, respectively as substituent groups to position 4 of C ring of a podophyllotoxin or 4┍d demethyl-epipodophyllotoxin, obtaining a podophyllotoxin derivative as shown in formula (V) with a significantly improved antitumour activity and reduced toxic side effects. Experiments of in vitro tumour cell activity inhibition indicate that the antitumour activity of the compound as shown in formula (V) of the present invention is significantly improved compared to that of the podophyllotoxin or 4┝d demethyl-epipodophyllotoxin.

14 Claims, 2 Drawing Sheets

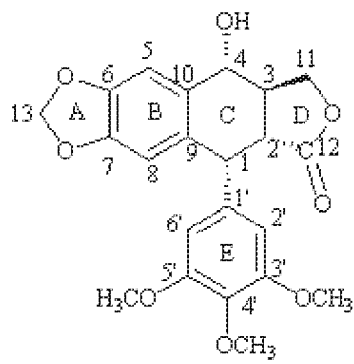
Podophyllotoxin

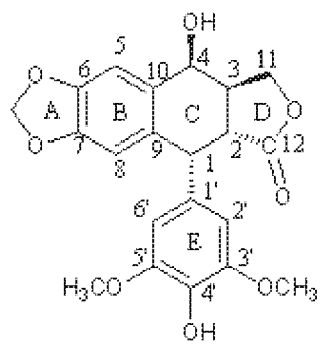
4'-Demethylepipodophyllotoxin

Figure 1

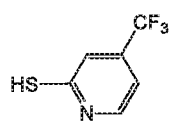

4-trifluoromethylpyridin-2-thiol
(1)

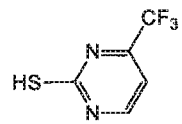

4-trifluoromethyl-2-mercaptopyrimidine
(2)

para-fluorothiophenol
(3)

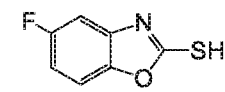

2-mercapto-5-fluorobenzothiazole
(4)

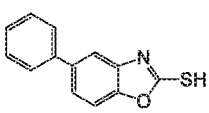

2-mercapto-5-fluorobenzoxazole
(5)

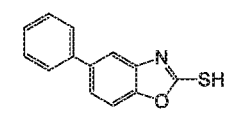

2-mercapto-5-phenyl benzoxazole
(6)

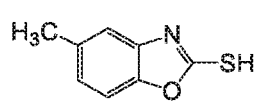

2-mercapto-5-methyl benzoxazole
(7)

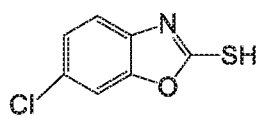

6-chlorobenzoxazol-2-thiol
(8)

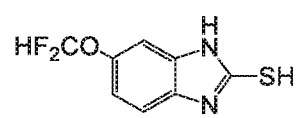

5-Difluoromethoxy-2-mercapto-1H-benzimidazole
(9)

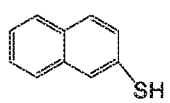

2-naphthalenethiol
(10)

1H-imidazole and pyridine (4,5-B)-2-mercaptan
(11)

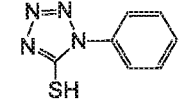

1-Phenyl-1H-tetrazole-5-thiol
(12)

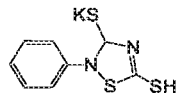

5-Mercapto-3-phenyl-1,3,4-thiadiazole
-2-thione Potassium Salt
(13)

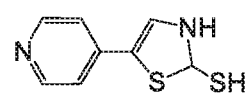

4-(4-Pyridinyl)thiazole-2-thiol
(14)

Figure 2

Formula(V)

4-SULFUR SUBSTITUTED PODOPHYLLOTOXIN DERIVATIVE AND PREPARATION METHOD THEREFOR AND USE THEREOF

CROSS-REFERENCE TO RELATED APPLICATIONS

The present application is a continuation of International Application No. PCT/CN2018/089832 filed Jun. 4, 2018, which claims priority from Chinese Patent Application No. 201710912793.8 filed Sep. 22, 2017, all of which are incorporated herein by reference.

TECHNICAL FIELD

The invention belongs to the field of podophyllotoxin derivatives, in particular to 4-sulfur substituted podophyllotoxin derivatives and a preparation method therefor, and the invention also relates to use of the 4-sulfur substituted podophyllotoxin derivatives in the preparation of antitumor drugs.

BACKGROUND ART

The structures of podophyllotoxin and demethylepipodophyllotoxin are shown as formula (I) and (II) in FIG. 1. Podophyllotoxin and 4′-demethylepipodophyllotoxin are natural active lead compounds with broad-spectrum antitumor activity extracted from podophyllotoxin plants (e.g. Sinopodophyllum hexandrum, Dickinsia hydrocotyloides, Dysosma versipellis, etc.). However, the clinical applications are limited due to their strong toxic side effects and poor bioavailability.

SUMMARY OF THE INVENTION

The first object of the present invention is to provide a class of 4-sulfur substituted podophyllotoxin derivatives having good antitumor activities;

the second object of the present invention is to provide a method for preparing the 4-sulfur substituted podophyllotoxin derivatives; and the third object of the invention is to apply the 4-sulfur substituted podophyllotoxin derivatives to the preparation of clinical antitumor drugs.

The above object of the present invention is achieved by the following technical solution: a class of 4-sulfur substituted podophyllotoxin derivatives with antitumor activity or pharmaceutically acceptable salts thereof, wherein the structural formula of the podophyllotoxin derivatives is shown as (V):

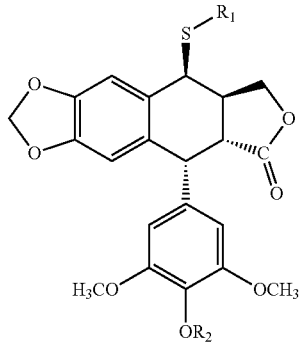

Formula (V)

Wherein $R_1$ is selected from

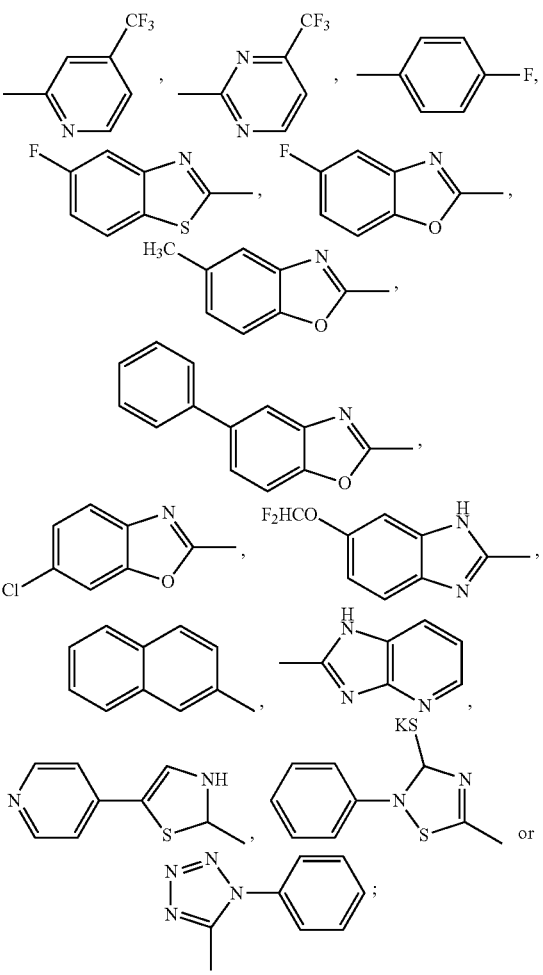

$R_2$ is hydrogen or —$CH_3$.

The invention adopts aromatic heterocyclic compounds having rigidity including 4-trifluoromethylpyridin-2-thiol, 4-trifluoromethyl-2-mercaptopyrimidine, para-fluorothiophenol, 5-fluorobenzothiazol-2-thiol, 5-fluorobenzoxazol-2-thiol, 5-phenylbenzoxazol-2-thiol, 5-methylbenzoxazol-2-thiol, 6-chlorobenzoxazol-2-thiol, 5-difluoromethoxybenzimidazol-2-thiol, 2-naphthalenethiol, 1H-imidazo[4,5-B]pyridin-2-thiol, 1-phenyltetrazol-5-thiol, 3-phenyl-1,3,4-thiadiazol-2(3H)thione potassium salt-5-thiol and 4-(4-pyridyl)thiazol-2-thiol, as shown in FIG. 2, which are used as substituent groups to facilitate the formation of the β-configuration of position-4 of the C ring in podophyllotoxin and 4′-demethylepipodophyllotoxin.

The method for preparing the compound shown in the formula (V) comprises the steps of: introducing a reaction monomer into position-4 of the C ring in podophyllotoxin or 4′-demethylepipodophyllotoxin through a nucleophilic substitution reaction, wherein the reaction monomer may be selected from the group consisting of 4-trifluoromethylpyridin-2-thiol, 4-trifluoromethyl-2-mercaptopyrimidine, para-fluorothiophenol, 5-fluorobenzothiazol-2-thiol, 5-fluorobenzoxazol-2-thiol, 5-phenylbenzoxazol-2-thiol, 5-methylbenzoxazol-2-thiol, 6-chlorobenzoxazol-2-thiol, 5-difluoromethoxybenzimidazol-2-thiol, 2-naphthalenethiol, 1H-imidazo[4,5-B]pyridin-2-thiol, 1-phenyltetrazol-5-thiol, 3-phenyl-1,3,4-thiadiazol-2(3H)thione potassium salt-5-thiol or 4-(4-pyridyl)thiazol-2-thiol.

In the present invention, the nucleophilic substitution reaction can be performed under the following conditions: dissolving podophyllotoxin or 4⊢d demethylepipodophyllotoxin in an organic solvent, adding the reaction monomer, followed by stirring, wherein the organic solvent may be a nucleophile which may be selected from trifluoroacetic acid, methanesulfonyl chloride or boron trifluoride diethyl ether.

In the present invention, the molar ratio of podophyllotoxin or 4⊡d demethylepipodophyllotoxin to the reaction monomer in the nucleophilic substitution reaction may be 1:1-10, for example 1:1-8, for example 1:1.

In the present invention, the temperature in nucleophilic substitution reaction may be −20-40° C., for example −20-20° C.

In the present invention, the temperature in nucleophilic substitution reaction may also be −10-10° C., for example 0-10° C.

The preparation method further comprises the steps of: pouring the reaction solution after the nucleophilic substitution reaction into deionized water, followed by separating out and filtering, and drying a filter cake to obtain 4-sulfur substituted podophyllotoxin derivatives crude products, wherein the volume of the deionized water may be 20-50 times that of the reaction solution after the nucleophilic substitution.

The preparation method further comprises the steps of: sequentially separating the crude products by using silica gel column chromatography and gel column chromatography to obtain purified 4-sulfur substituted podophyllotoxin derivatives products.

Preferably, the separation method using the silica gel column chromatography comprises the steps of: (1) the silica gel column chromatography including normal phase silica gel column chromatography or reverse phase silica gel column chromatography, packing the normal phase silica gel after stirring evenly with a low-polarity organic solvent, and equilibrating the column with an eluent, wherein the eluent is preferably the system of chloroform and acetone in a volume ratio of 40:1; packing the reverse phase silica gel after stirring evenly with methanol, and equilibrating the column with an eluent, wherein the eluent is preferably the system of methanol and water in a volume ratio of 60:1; and (2) dissolving a sample to be separated and purified with an eluent, performing sample loading and adsorption, eluting with an eluent, collecting the eluent, evaporating the sample, and performing recrystallization.

Preferably, the gel column chromatography separation method comprises the steps of: (1) soaking the gel with methanol; packing the treated gel into a column, and equilibrating with methanol; and (2) dissolving a sample preliminarily separated by silica gel column chromatography in methanol, performing sample loading and adsorption, eluting with methanol, collecting the eluant, evaporating the solvent in the sample, and performing recrystallization.

The in-vitro tests for inhibition of cell activity of HepG2, HeLa and HL-7702 show that the antitumor activity of the compound of the formula (V) prepared by the invention is significantly improved compared with that of podophyllotoxin or 4⊡d demethylepipodophyllotoxin. The test results show that the compound of the formula (V) can be prepared into an antitumor drug and is clinically applied to antitumor treatment.

The antitumor pharmaceutical composition provided by the invention comprises an effective amount of a compound of formula (V) or a salt thereof and a pharmaceutically acceptable carrier, that is, the pharmaceutically acceptable amount of the compound of formula (V) or the salt thereof and the pharmaceutically acceptable carrier are formulated and prepared into any type of suitable pharmaceutical composition according to a conventional formulation method in the art. In general, the pharmaceutical compositions are suitable for oral and injectable administration, as well as other methods of administration, for example transdermal administration. The pharmaceutical compositions may be in the form of tablets, capsules, powders, granules, lozenges, suppositories, or liquid preparations such as oral liquids or sterile parenteral suspensions. The composition may be in the form of large or small volume injection, lyophilized powder injection, sterile powder subpackage and the like. In order to achieve consistency of administration, the pharmaceutical compositions of the present invention are preferably in a single dosage form. Single dose forms for oral administration may be tablets and capsules and may contain conventional excipients such as binding agents, for example syrup, acacia gum, gelatin, sorbitol, tragacanth or polyvinylpyrrolidone; fillers such as lactose, sugar, corn starch, calcium phosphate, sorbitol or glycine; tabletting lubricants such as magnesium stearate; disintegrants, such as starch, polyvinylpyrrolidone, sodium starch glycolate or microcrystalline cellulose, or pharmaceutically acceptable wetting agents, such as sodium lauryl sulfate.

BRIEF DESCRIPTION OF THE DRAWINGS

FIG. 1 is a structural formula of podophyllotoxin and 4 ⊡d demethylepipodophyllotoxin;

FIG. 2 is a structural formula of 4-trifluoromethylpyridin-2-thiol, 4-trifluoromethyl-2-mercaptopyrimidine, para-fluorothiophenol, 5-fluorobenzothiazol-2-thiol, 5-fluorobenzoxazol-2-thiol, 5-phenylbenzoxazol-2-thiol, 5-methylbenzoxazol-2-thiol, 6-chlorobenzoxazol-2-thiol, 5-difluoromethoxybenzimidazol-2-thiol, 2-naphthalenethiol, 1H-imidazo [4,5-B] pyridin-2-thiol, 1-phenyltetrazol-5-thiol, 3-phenyl-1,3,4-thiadiazol-2(3H)thione potassium salt-5-thiol, and 4-(4-pyridyl)thiazol-2-thiol.

DETAILED DESCRIPTION OF THE INVENTION

Figure 3:
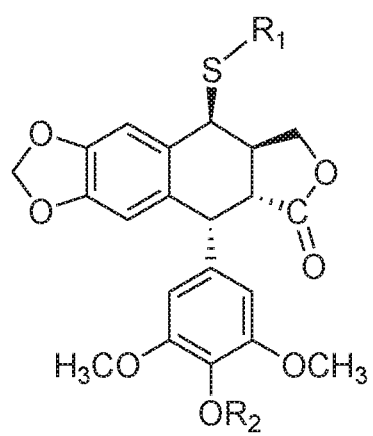
FIG. 3 is a structural formula of a compound of formula (V) of the present invention.

Hereinafter, the technical solution of the present invention will be further described through specific examples.

The materials and equipment employed in the present invention, unless otherwise specified, are either commercially available or commonly used in the art, and the methods of the examples, unless otherwise specified, are conventional methods in the art.

Test Materials

1. Podophyllotoxin and 4 ⊡d demethylepipodophyllotoxin: both purchased from Xi ª an Helin Bioengineering Co., Ltd.;

2. 4-trifluoromethylpyridin-2-thiol, 4-trifluoromethyl-2-mercaptopyrimidine, para-fluorothiophenol, 5-fluorobenzothiazol-2-thiol, 5-fluorobenzoxazol-2-thiol, 5-phenylbenzoxazol-2-thiol, 5-methylbenzoxazol-2-thiol, 6-chlorobenzoxazol-2-thiol, 5-difluoromethoxybenzimidazol-2-thiol, 2-naphthalenethiol, 1H-imidazo [4,5-B] pyridin-2-thiol, 1-phenyltetrazol-5-thiol, 3-phenyl-1,3,4-thiadiazol-2(3H)thione potassium salt-5-thiol, 4-(4-pyridyl)thiazol-2-thiol were purchased from Aladdin Reagent.

Example 1 Synthesis and Purification of 4-β-S-(4-trifluoromethylpyridin-2)-podophyllotoxin (Compound 1)

(1) Synthesis of 4-β-S-(4-trifluoromethylpyridin-2)-podophyllotoxin:

414 mg (1 mmol) of podophyllotoxin and 179 mg (1 mmol) of 4-trifluoromethylpyridin-2-thiol were dried under vacuum for 1 h, 15 ml of trifluoroacetic acid was added as a solvent in an ice bath, followed by stirring at atmospheric pressure for 1-3 h, chloroform acetone was used as a developing solvent to monitor the reaction endpoint; the reaction system was added into 20-50 times of volume of deionized water, followed by filtering, and a filter cake was collected, washed and dried to obtain a crude product.

(2) Separation and purification of 4β-S-(4-trifluoromethylpyridin-2)-podophyllotoxin: the separation and purification were performed using silica gel column chromatography and gel column chromatography:

(A) A separation was performed through a normal phase silica gel column (normal phase silica gel: China Qingdao Haiyang Chemical Co., Ltd., HG/T2354-92; separation system: Buchi isocratic flash chromatography system; chromatographic column: Buchi glass column C-690 with a length of 460 mm and an inner diameter of 15 mm) or similar polar column; a chloroform:acetone=40:1 system was used as eluent, with the loading sample of 2 ml, and the constant flow rate of 1.0 ml/min; each 2 ml of eluent was collected as a fraction. The fractions were examined by normal phase silica gel thin layer (German Merck high performance silica gel thin layer) or similar polar thin layer; chloroform:acetone=2:1 system was used as a developing solvent, and fractions with an Rf value of 0.5 were combined; the combined samples were dried under vacuum and stored in a 4° C. refrigerator in the dark as samples to be purified.

(B) A separation was performed through gel column chromatography (gel: Sephadex LH-20; a separation column: a glass column with a length of 480 mm and an inner diameter of 30 mm); the treated Sephadex LH-20 gel was wet packed and equilibrated with methanol. A sample to be purified was dissolved in 6 ml of methanol, loaded at a flow rate of 0.6 ml/min for adsorption, and then eluted with 600 ml of methanol at a flow rate of 0.6 ml/min; each 10 ml of eluent was collected into a bottle as a fraction, and the fractions were examined by normal phase silica gel thin layer (German Merck high performance silica gel thin layer) or similar polar thin layer; chloroform:acetone=2:1 system was used as a developing solvent, and fractions with an Rf value of 0.5 were combined; the white powder sample obtained after vacuum drying was 4-β-S-(4-trifluoromethylpyridin-2-thiol)-podophyllotoxin.

Compound 1 4-β-S-(4-trifluoromethylpyridin-2-thiol)-podophyllotoxin:white powder, $C_{28}H_{24}F_3NO_7S$ $^1$H NMR (300 MHz, $CDCl_3$) δ 8.65 (s, 1H), 7.74 (d, J=8.7 Hz, 1H), 7.29 (d, J=8.1 Hz, 1H), 6.90 (s, 1H), 6.47 (s, 1H), 6.32 (s, 1H), 5.97 (d, J=1.2 Hz, 1H), 5.94 (d, J=1.1 Hz, 1H), 5.57 (d, J=4.2 Hz, 1H), 4.60 (d, J=5.5 Hz, 1H), 4.40-3.81 (m, 2H), 3.80 (s, 3H), 3.76 (s, 6H), 3.30-3.33 (m, 1H), 3.17 (dd, J=13.8, 5.2 Hz, 1H). $^{13}$C NMR (75 MHz, $CDCl_3$) δ 174.40, 162.78, 152.48 (2C), 148.06, 147.31, 146.07, 137.11, 135.38, 133.06, 132.47, 127.55, 123.45 (q, J=202.5 Hz), 123.35, 121.15, 109.88 (2C), 108.20 (2C), 101.48, 70.68, 60.67, 56.17 (2C), 53.35, 46.21, 43.64, 42.48. MS-ESI: 576.13[M+H]$^+$

Example 2 Synthesis and Purification of 4-β-S-(4-trifluoromethylpyridin-2)-4'-demethylepipodophyllotoxin (Compound 2)

(1) Synthesis of 4-β-S-(4-trifluoromethylpyridin-2)-4'-demethylepipodophyllotoxin: 400 mg (1 mmol) of 4'-demethylepipodophyllotoxin and 179 mg (1 mmol) of 4-trifluoromethylpyridin-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and Purification of 4-β-S-(4-trifluoromethylpyridin-2)-4'-demethylepipodophyllotoxin:

the separation and purification were performed using silica gel column chromatography and gel column chromatography in the same manner as in Example 1.

Compound 2 4-β-S-(4-trifluoromethylpyridin-2)-4'-demethylepipodophyllotoxin:white powder, $C_{27}H_{22}F_3NO_7S$ $^1$H NMR (300 MHz, $CDCl_3$) δ 8.80 (d, J=4.9 Hz, 1H), 7.38 (d, J=4.8 Hz, 1H), 6.93 (s, 1H), 6.48 (s, 1H), 6.33 (s, 2H), 5.97 (d, J=1.2 Hz, 1H), 5.95 (d, J=1.3 Hz, 1H), 5.39 (d, J=4.2 Hz, 1H), 4.61 (d, J=5.1 Hz, 1H), 4.40-3.82 (m, 2H), 3.80 (s, 3H), 3.77 (s, 6H), 3.3-3.28 (m, 1H), 3.22 (dd, J=13.7, 5.1 Hz, 1H). $^{13}$C NMR (751.14 Hz, $CDCl_3$) 174.13, 172.85, 159.78, 152.51, 148.25, 147.40, 137.25, 135.30, 132.59, 126.67, 120.35 (d, J=221.2 Hz), 112.63, 110.02, 108.36, 101.54, 70.30, 60.66, 56.24, 47.72, 43.62, 42.31, 36.86. MS-ESI: 577.12[M+H]$^+$

Example 3 Synthesis and Purification of 4-β-S-(4-trifluoromethylpyrimidin-2)-podophyllotoxin (Compound 3)

(1) Synthesis of 4-β-S-(4-trifluoromethylpyrimidin-2)-podophyllotoxin: 414 mg (1 mmol) of podophyllotoxin and 1472 mg (8 mmol) of 4-(trifluoromethyl)-2-mercaptopyrimidine were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4-β-S-(4-trifluoromethylpyrimidin-2)-podophyllotoxin: the separation and purification were performed using silica gel column chromatography and gel column chromatography in the same manner as in Example 1.

Compound 3 4-β-S-(4-trifluoromethylpyrimidin-2)-podophyllotoxin:white powder, $C_{27}H_{23}F_3N_2O_7S$ $^1$H NMR (300 MHz, $CDCl_3$) δ 8.80 (d, J=4.9 Hz, 1H), 7.38 (d, J=4.8 Hz, 1H), 6.93 (s, 1H), 6.48 (s, 1H), 6.33 (s, 2H), 5.97 (d, J=1.21 Hz, 1H), 5.95 (d, J=1.3 Hz, 1H), 5.39 (d, J=4.2 Hz, 1H), 4.61 (d, J=5.1 Hz, 1H), 4.40-3.82 (m, 2H), 3.80 (s, 3H), 3.77 (s, 6H), 3.3-3.28 (m, 1H), 3.22 (dd, J=13.7, 5.1 Hz, 1H). $^{13}$C NMR (75 MHz, $CDCl_3$) δ 174.13, 172.85, 159.78, 152.51 (2C), 148.25, 147.40, 137.25, 135.30, 132.59, 126.67, 120.35 (q, J=221.2 Hz), 112.63, 110.02 (2C) 108.36 (2C), 101.54, 70.30, 60.66, 56.24 (2C), 47.72, 43.62, 42.31, 36.86. MS-ESI: 563.11[M+H]$^+$

Example 4 Synthesis and Purification of 4-β-S-(4-trifluoromethylpyrimidin-2)-4⊟demethylepipodophyllotoxin (Compound 4)

(1) Synthesis of 4-β-S-(4-trifluoromethylpyrimidin-2)-4⊟demethylepipodophyllotoxin: 400 mg (1 mmol) of 4⊟demethylepipodophyllotoxin and 180 mg (1 mmol) of 4-(trifluoromethyl)-2-mercaptopyrimidine were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and Purification of 4-β-S-(4-trifluoromethylpyrimidin-2)-4⊟demethylepipodophyllotoxin:
the separation and purification were performed using silica gel column chromatography and gel column chromatography in the same manner as in Example 1.

Compound 4 4-β-S-(4-trifluoromethylpyrimidin-2)-4⊟demethylepipodophyllotoxin:white powder, $C_{26}H_{21}F_3N_2O_7S$ $^1$H NMR (300 MHz, CDCl$_3$) δ 8.82 (d, J=4.9 Hz, 1H), 7.40 (d, J=4.8 Hz, 1H), 6.94 (s, 1H), 6.49 (s, 1H), 6.35 (s, 2H), 5.99 (d, J=1.2 Hz, 1H), 5.97 (d, J=1.3 Hz, 1H), 5.48 (s, 1H), 5.39 (d, J=4.2 Hz, 1H), 4.62 (d, J=5.1 Hz, 1H), 4.43-3.82 (m, 2H), 3.81 (s, 6H), 3.35-3.25 (m, 1H), 3.21 (dd, J=13.7, 5.1 Hz, 1H). $^{13}$C NMR (100 MHz, CDCl$_3$) δ 174.20, 172.87, 159.77, 148.24, 147.35, 146.36 (2C), 134.12, 132.86, 132.78, 130.80, 126.68, 119.88 (q, J=205.5 Hz), 112.62, 110.13, 109.98, 108.02 (2C), 101.51, 70.28, 56.45 (2C), 47.73, 43.46, 42.41, 36.79. MS-ESI: 525.13[M+H]$^+$

Example 5 Synthesis and Purification of 4β-S-(4-fluorobenzene-1)-podophyllotoxin (Compound 5)

(1) Synthesis of 4β-S-(4-fluorobenzene-1)-podophyllotoxin: 414 mg (1 mmol) of podophyllotoxin and 127 mg (1 mmol) of para-fluorothiophenol were dried under vacuum for 1 h, the mixture was stirred under atmospheric pressure for 1-3 h with 15 ml of trifluoroacetic acid as a solvent at −10° C., and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(4-fluorobenzene-1)-podophyllotoxin: the separation and purification were performed using silica gel column chromatography and gel column chromatography in the same manner as in Example 1.

Compound 5 4β-S-(4-fluorobenzene-1)-podophyllotoxin: white powder, $C_{28}H_{25}FO_7S$ $^1$H NMR (400 MHz, CDCl$_3$) δ 7.34-7.29 m, 1H), 7.10-7.04 (m, 2H), 6.95-6.92 (m, 1H), 6.94 (s, 1H), 6.46 (s, 1H), 6.27 (s, 2H), 5.98 (d, J=1.3 Hz, 1H), 5.96 (d, J=1.3 Hz, 1H), 4.85 (d, J=4.2 Hz, 1H), 4.58 (d, J=5.1 Hz, 1H), 4.18-4.09 (m, 2H), 3.78 (s, 3H), 3.74 (s, 6H) 3.33 (dd, J=13.7, 5.1 Hz, 1H), 3.24-3.21 (m, 1H). $^{13}$C NMR (101 MHz, CDCl$_3$) δ 174.26, 162.93 (d, $^1$J=248 Hz), 152.54 (2C), 148.15, 147.32, 138.35 (d, $^3$J=5 Hz), 137.22, 135.39, 132.07, 130.85, 127.90, 124.22, 115.55 (d, $^2$J=23 Hz), 114.01 (d, $^2$J=19 Hz), 109.97 (2C), 108.24 (2C), 101.57, 69.40, 60.37, 56.22 (2C), 49.37, 43.56, 41.88, 37.73. MS-ESI: 525.13[M+M]$^+$

Example 6 Synthesis and Purification of 4β-S-(4-fluorobenzene-1)-4⊟demethylepipodophyllotoxin (Compound 6)

(1) Synthesis of 4β-S-(4-fluorobenzene-1)-4⊟demethylepipodophyllotoxin: 400 mg (1 mmol) of 4⊟demethylepipodophyllotoxin and 127 mg (1 mmol) of para-fluorothiophenol were dried under vacuum for 1 h, the mixture was stirred under vacuum for 1-3 h with 15 ml of trifluoroacetic acid as a solvent at 15° C., and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(4-fluorobenzene-1)-4⊟demethylepipodophyllotoxin: the separation and purification were performed using silica gel column chromatography and gel column chromatography in the same manner as in Example 1.

Compound 6 4β-S-(4-fluorobenzene-1)-4⊟demethylepipodophyllotoxin:white powder, $C_{27}H_{23}FO_7S$ $^1$H NMR (400 MHz, CDCl$_3$) δ 7.30 (td, J=8.1, 6.0 Hz, 1H), 7.13-7.03 (m, 2H), 6.97-6.92 (m, 1H), 6.93 (s, 1H), 6.46 (s, 1H), 6.29 (s, 2H), 5.98 (d, J=1.3 Hz, 1H), 5.95 (d, J=1.3 Hz, 1H), 5.42 (s, 1H), 4.84 (d, J=4.2 Hz, 1H), 4.57 (d, J=5.1 Hz, 1H), 4.17-4.15 (m, 2H), 3.77 (s, 6H), 3.32 (dd, J=13.7, 5.1 Hz, 1H), 3.27-3.15 (m, 1H). $^{13}$C NMR (101 MHz, CDCl$_3$) δ 174.36, 162.83 (d, $^1$J=249 Hz), 148.15, 147.29, 146.39 (2C), 138.39 (d, $^3$J=8 Hz), 134.09, 132.26, 130.8, 130.7, 127.93, 124.25, 115.5 (d, $^2$J=23 Hz), 114.05 (d, $^2$J=21 Hz), 110.0, 109.97, 107.93 (2C), 101.58, 69.43, 56.46 (2C), 49.41, 43.45, 42.03, 37.73. MS-ESI: 511.14[M+H]$^+$

Example 7 Synthesis and Purification of 4β-S-(5-fluorobenzothiazol-2)-podophyllotoxin (Compound 7)

(1) Synthesis of 4β-S-(5-fluorobenzothiazol-2)-podophyllotoxin: 414 mg (1 mmol) of podophyllotoxin and 184 mg (1 mmol) of 5-fluorobenzothiazol-2-thiol were dried under vacuum for 1 h, the mixture was stirred under vacuum for 1-3 h with 15 ml of trifluoroacetic acid as a solvent at 4° C., and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(5-fluorobenzothiazol-2)-podophyllotoxin: the separation and purification were performed using silica gel column chromatography and gel column chromatography in the same manner as in Example 1.

Compound 7 4β-S-(5-fluorobenzothiazol-2)-podophyllotoxin:white powder, $C_{29}H_{24}FNO_7S_2$ $^1$N NMR (400 MHz, CDCl$_3$) δ 7.76 (dd, J=8.9, 4.7 Hz, 1H), 7.45 (dd, J=7.9, 2.5 Hz, 1H), 7.15 (td, J=8.9, 2.5 Hz, 1H), 6.98 (s, 1H), 6.47 (s, 1H), 6.32 (s, 2H), 5.96 (d, J=1.0 Hz, 1H), 5.94 (d, J=1.0 Hz, 1H), 5.70 (d, J=4.3 Hz, 1H), 4.59 (d, J=5.2 Hz, 1H), 4.44-3.97 (m, 2H), 3.79 (s, 3H), 3.75 (s, 6H), 3.43-3.27 (m, 1H), 3.18 (dd, J=13.7, 5.2 Hz, 1H). $^{13}$C NMR (101 MHz, CDCl$_3$) δ 174.27, 164.86 (d, J=2.9 Hz), 161.25, 158.81, 152.58, 149.27 (d, J=1.7 Hz), 148.47, 147.51, 137.23, 136.15 (d, J=11.1 Hz), 135.26, 132.70, 126.79, 122.17 (d, J=9.3 Hz), 114.81, 114.56, 110.04 (d, J=10.3 Hz), 108.27, 107.92, 107.65, 101.68, 70.73, 60.74, 56.25, 49.86, 43.69, 42.55, 37.11. MS-ESI: 582.15[M+H]⁺

Example 8 Synthesis and Purification of 4β-S-(5-fluorobenzothiazol-2)-4′-demethylepipodophyllotoxin (Compound 8)

(1) Synthesis of 4β-S-(5-fluorobenzothiazol-2)-4′-demethylepipodophyllotoxin: 400 mg (1 mmol) of 4′-demethylepipodophyllotoxin and 184 mg (1 mmol) of 5-fluorobenzothiazol-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(5-fluorobenzothiazol-2)-4′-demethylepipodophyllotoxin: the separation and purification were performed using silica gel column chromatography and gel column chromatography in the same manner as in Example 1.

Compound 8 4β-S-(5-fluorobenzothiazol-2)-4′-demethylepipodophyllotoxin:white powder, $C_{28}H_{22}FNO_7S_2$ ¹H NMR (400 MHz, CDCl₃) δ 7.77 (dd, J=8.9, 4.7 Hz, 1H), 7.46 (dd, J=8.0, 2.5 Hz, 1H), 7.17 (td, J=8.9, 2.6 Hz, 1H), 6.98 (s, 1H), 6.48 (s, 1H), 6.32 (s, 2H), 5.97 (d, J=1.2 Hz, 1H), 5.95 (d, J=1.2 Hz, 1H), 5.71 (d, J=4.3 Hz, 1H), 5.50 (s, 1H), 4.60 (d, J=5.1 Hz, 1H), 4.43-3.88 (m, 2H), 3.78 (s, 6H), 3.42-3.28 (m, 1H), 3.17 (dd, J=13.7, 5.2 Hz, 1H). ¹³C NMR (101 MHz, CDCl₃) δ 174.31, 164.90 (d, J=3.0 Hz), 161.27, 158.82, 149.30, 148.46, 147.46, 146.45, 136.16 (d, J=11.1 Hz), 134.15, 132.91, 130.72, 126.81, 122.17 (d, J=9.3 Hz), 114.81, 114.57, 110.03 (d, J=2.6 Hz), 107.94 (d, J=4.7 Hz), 107.65, 101.65, 70.70, 56.48, 49.87, 43.53, 42.66, 37.04. MS-ESI: 568.75[M+H]⁺

Example 9 Synthesis and Purification of 4β-S-(5-fluorobenzoxazol-2)-podophyllotoxin (Compound 9)

(1) Synthesis of 4β-S-(5-fluorobenzoxazol-2)-podophyllotoxin: 414 mg (1 mmol) of podophyllotoxin and 169 mg (1 mmol) of 5-fluorobenzoxazol-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(5-fluorobenzoxazol-2)-podophyllotoxin: the separation and purification were performed using silica gel column chromatography and gel column chromatography in the same manner as in Example 1.

Compound 9 4β-S-(5-Fluorobenzoxazol-2)-podophyllotoxin:white powder, $C_{29}H_{24}FNO_8S$ ¹H NMR (400 MHz, CDCl₃) δ 7.40 (dd, J=8.9, 4.2 Hz, 1H), 7.28 (dd, J=8.1, 2.5 Hz, 1H), 7.03 (dd, J=9.1, 2.6 Hz, 1H), 6.99 (s, 1H), 6.50 (s, 1H), 6.31 (s, 2H), 5.99 (d, J=1.2 Hz, 1H), 5.98 (d, J=1.2 Hz, 1H), 5.55 (d, J=4.2 Hz, 1H), 4.63 (d, J=5.2 Hz, 1H), 4.50 (dd, J=9.1, 7.4 Hz, 1H), 3.95 (dd, J=10.3, 9.3 Hz, 1H), 3.81 (s, 3H), 3.77 (s, 6H), 3.43-3.33 (m, 1H), 3.17 (dd, J=13.7, 5.2 Hz, 1H). ¹³CNMR (101 MHz, CDCl₃) δ 173.99, 165.70, 158.92, 155.03, 148.67, 148.13, 147.59, 146.46, 142.08, 134.18, 132.91, 130.52, 126.31, 112.07, 111.81, 110.41, 110.02, 107.89, 105.40, 105.14, 101.73, 70.32, 60.76, 56.25, 49.92, 43.69, 42.45, 36.89, 29.69. MS-ESI: 566.25[H+H]⁺

Example 10 Synthesis and Purification of 4β-S-(5-fluorobenzoxazol-2)-4′-demethylepipodophyllotoxin (Compound 10)

(1) Synthesis of 4β-S-(5-fluorobenzoxazol-2)-4′-demethylepipodophyllotoxin: 400 mg (1 mmol) of 4′-demethylepipodophyllotoxin and 169 mg (1 mmol) of 5-fluorobenzoxazol-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(5-fluorobenzoxazol-2)-4′-demethylepipodophyllotoxin: the separation and purification were performed using silica gel column chromatography and gel column chromatography in the same manner as in Example 1.

Compound 10 4β-S-(5-fluorobenzoxazol-2)-4′-demethylepipodophyllotoxin:white powder, $C_{28}H_{22}FNO_8S$ ¹H NMR (400 MHz, CDCl₃) δ 7.40 (dd, J=8.9, 4.2 Hz, 1H), 7.28 (dd, J=8.2, 2.5 Hz, 1H), 7.02 (dd, J=9.1, 2.6 Hz, 1H), 6.99 (s, 1H), 6.50 (s, 1H), 6.31 (s, 2H), 5.99 (d, J=1.3 Hz, 1H), 5.97 (d, J=1.2 Hz, 1H), 5.55 (d, J=4.2 Hz, 1H), 5.44 (s, 1H), 4.62 (d, J=5.2 Hz, 1H), 4.48 (dd, J=9.1, 7.4 Hz, 1H), 3.95 (dd, J=10.3, 9.3 Hz, 1H), 3.79 (s, 6H), 3.43-3.31 (m, 1H), 3.17 (dd, J=13.7, 5.2 Hz, 1H). ¹³C NMR (101 MHz, CDCl₃) δ 173.99, 165.70, 158.92, 155.03, 148.67, 148.13, 147.59, 146.46, 142.08, 134.18, 132.91, 130.52, 126.31, 112.07, 111.81, 110.41, 110.02, 107.89, 105.40, 105.14, 101.73, 70.30, 56.46, 49.92, 43.53, 42.56, 36.82. MS-ESI: 552.68[M+H]⁺

Example 11 Synthesis and Purification of 4β-S-(5-phenylbenzoxazol-2)-podophyllotoxin (Compound 11)

(1) Synthesis of 4β-S-(5-phenylbenzoxazol-2)-podophyllotoxin: 414 mg (1 mmol) of podophyllotoxin and 1816 mg (8 mmol) of 5-phenylbenzoxazol-2-thiol were dried under vacuum for 1 h, the mixture was stirred under atmospheric pressure for 1-3 h with 15 ml of trifluoroacetic acid as a solvent at −10° C., and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(5-phenylbenzoxazol-2)-podophyllotoxin: the separation and purification were performed using silica gel column chromatography and gel column chromatography in the same manner as in Example 1.

Compound 11 4β-S-(5-phenylbenzoxazol-2)-podophyllotoxin:white powder, $C_{35}H_{29}FNO_8S$ ¹H NMR (400 MHz, CDCl₃) δ 7.78 (t, J=1.0 Hz, 1H), 7.61-7.57 (m, 2H), 7.52 (d, J=1.1 Hz, 7.46 (t, J=7.6 Hz, 2H), 7.41-7.34 (m, 1H), 7.02 (s, 1H), 6.50 (s, 1H), 6.32 (s, 2H), 5.99 (d, J=1.1 Hz, 1H), 5.97 (d, J=1.2 Hz, 1H), 5.60 (d, J=4.2 Hz, 1H), 4.63 (d, J=5.2 Hz, 1H), 4.55-3.98 (m, 2H), 3.81 (s, 3H), 3.77 (s, 6H), 3.46-3.34 (m, 1H), 3.21 (dd, J=13.8, 5.2

Hz, 1H). $^{13}$C NMR (100 MHz, CDCl$_3$) δ 174.01, 164.32, 152.64, 151.35, 148.64, 147.62, 141.90, 140.73, 138.66, 137.28, 135.10, 132.72, 128.91, 127.41, 126.45, 124.10, 116.97, 110.29, 109.91, 108.22, 101.74 70.42, 60.77, 56.25, 49.83, 43.71, 42.46, 36.95. NIS-ESI: 664.61[M+Na]$^+$

Example 12 Synthesis and Purification of 4β-S-(5-phenylbenzoxazol-2)-4 ⊡d demethylepipodophyllotoxin (Compound 12)

(1) Synthesis of 4β-S-(5-phenylbenzoxazol-2)-4 ⊡d demethylepipodophyllotoxin: 400 mg (1 mmol) of 4 ⊡d demethylepipodophyllotoxin and 227 mg (1 mmol) of 5-phenylbenzoxazol-2-thiol were dried under vacuum for 1 h, the mixture was stirred under vacuum for 1-3 h with 15 ml of trifluoroacetic acid as a solvent at 20° C., and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(5-phenylbenzoxazol-2)-4 ⊡d demethylepipodophyllotoxin: the separation and purification were performed using silica gel column chromatography and gel column chromatography in the same manner as in Example 1.

Compound 12 4β-S-(5-phenylbenzoxazol-2)-4 ⊡d demethylepipodophyllotoxin:white powder, C$_{34}$H$_{27}$FNO$_8$S $^1$H NMR (400 MHz, CDCl$_3$) δ 7.78 (t, J=1.0 Hz, 1H), 7.61-7.57 (m, 2H), 7.52 (d, J=1.1 Hz, 2H), 7.46 (t, J=7.6 Hz, 2H), 7.41-7.34 (m, 1H), 7.02 (s, 1H), 6.50 (s, 1H), 6.32 (s, 2H), 5.99 (d, J=1.1 Hz, 1H), 5.97 (d, J=1.2 Hz, 1H), 5.60 (d, J=4.2 Hz, 1H), 4.63 (d, J=5.2 Hz, 1H), 4.55-3.98 (m, 2H), 3.81 (s, 3H), 3.77 (s, 6H), 3.46-3.34 (m, 1H), 3.21 (dd, J=13.8, 5.2 Hz, 1H). $^{13}$C NMR (100 MHz, CDCl$_3$) δ 174.01, 164.32, 152.64, 151.35, 148.64, 147.62, 141.90, 140.73, 138.66, 137.28, 135.10, 132.72, 128.91, 127.41, 126.45, 124.10, 116.97, 110.29, 109.91, 108.22, 101.74, 70.42, 60.77, 56.25, 49.83, 43.71, 42.46, 36.95. MS-ESI: 664.61 [H+Na]$^+$

Example 13 Synthesis and Purification of 4β-S-(5-methylbenzoxazol-2)-podophyllotoxin (Compound 13)

(1) Synthesis of 4β-S-(5-methylbenzoxazol-2)-podophyllotoxin: 414 mg (1 mmol) of podophyllotoxin and 1320 mg (8 mmol) of 5-methylbenzoxazol-2-thiol were dried under vacuum for 1 h, the mixture was stirred under atmospheric pressure for 1-3 h with 15 ml of trifluoroacetic acid as a solvent at −10° C., and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(5-methylbenzoxazol-2)-podophyllotoxin: the separation and purification were performed using silica gel column chromatography and gel column chromatography in the same manner as in Example 1.

Compound 13 4β-S-(5-methylbenzoxazol-2)-podophyllotoxin:white powder, C$_{30}$H$_{27}$FNO$_8$S $^1$H NMR (400 MHz, CDCl$_3$) δ 7.39-7.27 (m, 2H), 7.09 (dd, J=8.3, 1.1 Hz, 1H), 700 (s, 1H), 6.48 (s, 1H), 6.31 (s, 2H), 5.98 (d, J=1.2 Hz, 1H), 5.96 (d, J=1.2 Hz, 1H), 5.56 (d, J=4.2 Hz, 1H), 4.61 (d, J=5.2 Hz, 1H), 4.5-3.96 (m, 2H), 3.80 (s, 3H), 3.76 (s, 6H), 3.43-330 (m, 1H), 3.19 (dd, J=13.8, 5.2 Hz, 1H), 2.45 (s, 3H). $^{13}$C NMR (100 MHz, CDCl$_3$) δ 174.02, 163.54, 152.62, 150.06, 148.59, 147.58, 141.44, 137.32, 135.13, 134.58, 132.68, 126.56, 125.51, 118.48, 110.04, 109.53, 108.27, 101.70, 70.39, 60.74, 56.24, 49.63, 43.71, 42.41, 36.94. MS-ESI: 562.15[M+H]$^+$

Example 14 Synthesis and Purification of 4β-S-(5-methylbenzoxazol-2)-4 ⊡d demethylepipodophyllotoxin (Compound 14)

(1) Synthesis of 4β-S-(5-methylbenzoxazol-2)-4 ⊡d demethylepipodophyllotoxin: 400 mg (1 mmol) of 4 ⊡d demethylepipodophyllotoxin and 165 mg (1 mmol) of 5-methylbenzoxazol-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(5-methylbenzoxazol-2)-4 ⊡d demethylepipodophyllotoxin: the separation and purification were performed using silica gel column chromatography and gel column chromatography in the same manner as in Example 1.

Compound 14 4β-S-(5-methylbenzoxazol-2)-4 ⊡d demethylepipodophyllotoxin:white powder, C$_{29}$H$_{25}$FNO$_8$S $^1$H NMR (400 MHz, CDCl$_3$) δ 7.41-7.29 (m, 2H), 7.10 (dd, J=8.3, 1.5 Hz, 1H), 7.00 (s, 1H), 6.49 (s, 1H), 6.32 (s, 2H), 5.99 (d, J=1.2 Hz, 1H), 5.97 (d, J=1.2 Hz, 1H), 5.56 (d, J=42 Hz, 1H), 5.44 (s, 1H), 4.61 (d, J=5.1 Hz, 1H), 4.49-3.93 (m, 2H), 3.79 (s, 6H), 3.45-3.28 (m, 1H), 3.18 (dd, J=13.7, 5.2 Hz, 1H), 2.46 (s, 3H). $^{13}$C NMR (100 MHz, CDCl$_3$) δ 174.09, 163.58, 152.34, 150.06, 148.58, 147.54, 146.46, 141.44, 134.59, 134.16, 132.86, 130.63, 126.57, 125.51, 118.48, 110.03, 109.53, 107.91, 101.67, 70.37, 56.46, 49.64, 43.55, 42.53, 36.87. MS-ESI: 548.32[M+H]$^+$

Example 15 Synthesis and Purification of 4β-S-(6-chlorobenzoxazol-2)-podophyllotoxin (Compound 15)

(1) Synthesis of 4β-S-(6-chlorobenzoxazol-2)-podophyllotoxin: 414 mg (1 mmol) of podophyllotoxin and 201 mg (1 mmol) of 6-chlorobenzoxazol-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(6-chlorobenzoxazol-2)-podophyllotoxin: the separation and purification were performed using silica gel column chromatography and gel column chromatography in the same manner as in Example 1.

Compound 15 4β-S-(6-chlorobenzoxazol-2)-podophyllotoxin:white powder, C$_{29}$H$_{24}$ClNO$_7$S$_2$ $^1$H NMR (400 MHz, CDCl$_3$) δ 7.53-7.43 (m, 2H), 7.30 (dd, J=8.3, 2.1 Hz, 1H), 6.99 (s, 1H), 6.48 (s, 1H), 6.30 (s, 2H), 5.98 (d, J=1.2 Hz, 1H), 5.96 (d, J=1.2 Hz, 1H), 5.53 (d, J=4.2 Hz, 1H), 4.61 (d, J=5.2 Hz, 1H), 4.49 (dd, J=9.1, 7.4 Hz, 1H), 3.95 (dd, J=10.3, 9.3 Hz, 1H), 3.80 (s, 3H), 3.75 (s, 6H), 3.41-3.32 (m, 1H), 3.18 (dd, J=13.8, 5.2 Hz, 1H). $^{13}$C NMR (100 MHz, CDCl$_3$) δ 173.87, 164.54, 152.64, 151.89, 148.69, 147.64, 140.07, 137.37, 135.01, 132.74, 130.23, 126.28, 125.31, 118.86, 110.88, 110.03, 108.28, 101.74, 70.29, 60.74, 56.30, 50.02, 43.68, 42.44, 36.90. MS-ESI: 583.14[M+H]$^+$ Example 16 Synthesis and Purification of 4β-S-(6-chlorobenzoxazol-2)-4'd demethylepipodophyllotoxin (Compound 16)

(1) Synthesis of 4β-S-(6-chlorobenzoxazol-2)-4'd demethylepipodophyllotoxin: 400 mg (1 mmol) of 4'd demethylepipodophyllotoxin and 1472 mg (8 mmol) of 6-chlorobenzoxazol-2-thiol were dried under vacuum for 1 h, the mixture was stirred under atmospheric pressure for 1-3 h with 15 ml of trifluoroacetic acid as a solvent at −10° C., and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(6-chlorobenzoxazol-2)-4'd demethylepipodophyllotoxin: the separation and purification were performed using silica gel column chromatography and gel column chromatography in the same manner as in Example 1.

Compound 16 4β-S-(6-chlorobenzoxazol-2)-4'd demethylepipodophyllotoxin: white powder, $C_{28}H_{22}ClNO_7S_2$ $^1$H NMR (400 MHz, CDCl$_3$) δ 7.53-7.42 (m, 2H), 7.30 (dd, J-=8.3, 2.2 Hz, 1H), 6.99 (s, 1H), 6.49 (s, 1H), 6.31 (s, 2H), 5.99 (d, J=1.3 Hz, 1H), 5.97 (d, J=1.2 Hz, 1H), 5.53 (d, J=4.2 Hz, 1H), 5.46 (s, 1H), 4.61 (d, J=5.2 Hz, 1H), 4.47 (dd, J=9.1, 7.4 Hz, 1H), 3.95 (dd, J=10.3, 9.3 Hz, 1H), 3.78 (s, 6H), 3.44-3.29 (m, 1H), 3.17 (dd, J=13.7, 5.2 Hz, 1H). $^{13}$CNMR (100 MHz, CDCl$_3$) δ 173.94, 164.58, 151.89, 148.69, 147.60, 146.49, 140.07, 134.23, 132.93, 130.52, 130.24, 126.29, 125.31, 118.86, 110.89, 110.02, 107.94, 101.72, 70.27, 56.44, 50.03, 43.53, 42.55, 36.83. MS-ESI: 569.21[M+H]$^+$ Example 17 Synthesis and Purification of 4β-S-(5-difluoromethoxybenzimidazol-2)-podophyllotoxin (Compound 17)

(1) Synthesis of 4β-S-(5-difluoromethoxybenzimidazol-2)-podophyllotoxin: 414 mg (1 mmol) of podophyllotoxin and 216 mg (1 mmol) of 5-difluoromethoxybenzimidazol-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(5-difluoromethoxybenzimidazol-2)-podophyllotoxin: the separation and purification were performed using silica gel column chromatography and gel column chromatography in the same manner as in Example 1.

Compound 17 4β-S-(5-difluoromethoxybenzimidazol-2)-podophyllotoxin: white powder, $C_{30}H_{26}F_2N_2O_8S$ $^1$H NMR (400 MHz, CDCl$_3$) δ 9.97 (d, J=20.4 Hz, 1H) 7.56-7.53, 7.26-7.24 (m, 1H), 7.11, 7.39 (dd, 1H), 7.03-6.99 (m, 1H), 6.99 (s, 1H), 6.67-6.48 (m, 1H), 6.46 (s, 1H), 6.30 (s, 2H), 5.96 (d, J=1.1 Hz, 1H), 5.94 (d, J=1.1 Hz, 1H), 5.71 (d, J=3.5 Hz, 1H), 4.60 (d, J=5.2 Hz, 1H), 4.43 (t, J=7.6 Hz, 1H), 3.90 (t, J=9.7 Hz, 1H), 3.80 (s, 3H), 3.73 (s, 6H), 3.45-3.29 (m, 1H), 3.21 (dd, J=13.8, 5.2 Hz, 1H). $^{13}$C NMR (100 MHz, CDCl$_3$) δ 174.82, 152.51, 150.94, 150.20, 148.37, 147.45, 146.63, 143.78, 141.09, 136.93, 135.31, 134.91, 132.40, 127.11, 118.88, 118.45, 116.29, 116.21, 115.89, 115.18, 113.89, 110.59, 110.00, 109.84, 109.43, 108.03, 102.43, 101.62, 70.80, 60.72, 56.12, 53.388, 48.79, 43.69, 42.54, 36.95. MS-ESI: 635.34[M+Na]$^+$ Example 18 Synthesis and Purification of 4β-S-(5-difluoromethoxybenzimidazol-2)-4'd demethylepipodophyllotoxin (Compound 18)

(1) Synthesis of 4β-S-(5-difluoromethoxybenzimidazol-2)-4'd demethylepipodophyllotoxin: 400 mg (1 mmol) of 4'd demethylepipodophyllotoxin and 216 mg (1 mmol) of 5-difluoromethoxybenzimidazol-2-thiol were dried under vacuum for 1 h, the mixture was stirred under vacuum for 1-3 h with 15 ml of methanesulfonyl chloride as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and Purification of 4β-S-(5-difluoromethoxybenzimidazol-2)-4'd demethylepipodophyllotoxin: the separation and purification were performed using silica gel column chromatography and gel column chromatography in the same manner as in Example 1.

Compound 18 4β-S-(5-difluoromethoxybenzimidazol-2)-4'd demethylepipodophyllotoxin: white powder, $C_{29}H_{24}F_2N_2O_8S$ $^1$H NMR (300 MHz, CDCl$_3$) δ 12.91 (s, 1H), 8.35 (s, 1H), 7.58-7.56, (m, 1H), 7.45-7.43 (m, 1H), 7.10 (s, 1H), 7.02 (s, 1H), 6.99 (s, 1H), 6.20 (s, 2H), 5.78 (d, J=1.1 Hz, 1H), 5.77 (d, J=1.1 Hz, 1H), 5.66 (d, J=3.5 Hz, 1H), 4.55 (d, J=5.2 Hz, 1H), 4.40-3.86 (m, 1H), 3.67 (s, 6H), 3.45-3.29 (m, 1H), 3.21 (dd, J=13.8, 5.2 Hz, 1H). $^{13}$C NMR (75 MHz, CDCl$_3$) δ 174.38, 151.93, 151.13, 147.85, 147.48, 146.93, 146.58, 144.11, 141.32, 135.88, 135.03, 133.36, 133.15, 130.74, 128.22, 118.46, 117.31, 114.75, 114.07, 111.52, 110.19, 109.84, 109.40, 108.77, 108.39, 102.01, 101.77, 70.42, 56.32, 48.73, 43.12, 41.95, 31.04. MS-ESI: 621.13[M+Na]$^+$ Example 19 Synthesis and Purification of 4β-S-(naphthalen-2)-podophyllotoxin (Compound 19)

(1) Synthesis of 4β-S-(naphthalen-2)-podophyllotoxin: 414 mg (1 mmol) of podophyllotoxin and 160 mg (1 mmol) of 2-naphthalenethiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(naphthalene-2)-podophyllotoxin: the separation and purification were performed using silica gel column chromatography and gel column chromatography in the same manner as in Example 1.

Compound 19 4β-S-(Naphthalene-2)-podophyllotoxin: white powder, $C_{32}H_{28}O_7S$ $^1$H NMR (400 MHz, CDCl$_3$) δ 7.86-7.69 (m, 4H), 7.57-7.40 (m, 3H), 7.03 (s, 1H), 6.47 (s, 1H), 6.31 (s, 2H), 5.97 (d, J=1.2 Hz, 1H), 5.95 (d, J=1.3 Hz, 1H), 4.97 (d, J=4.3 Hz, 1H), 4.59 (d, J=5.2 Hz, 1H) 4.39-4.09 (m, 2H), 3.79 (s, 3H), 3.75 (s, 6H), 3.41 (dd, J=13.7, 5.2 Hz, 1H), 3.31-3.19 (m, 1H). $^{13}$C NMR (100 MHz, CDCl$_3$) δ 174.49, 152.54, 148.05, 147.30, 137.20, 135.58, 133.70, 133.32, 132.10, 132.06, 129.18, 128.51, 127.82, 127.45, 127.11, 127.05, 127.04, 126.39, 110.06, 108.31, 101.56, 69.58, 60.75, 56.26, 49.64, 43.68, 42.01, 38.01. MS-ESI: 586.14[M+K]$^+$

Example 20 Synthesis and Purification of 4β-S-(naphthalen-2)-4′-demethylepipodophyllotoxin (Compound 20)

(1) Synthesis of 4β-S-(naphthalen-2)-4′-demethylepipodophyllotoxin: 400 mg (1 mmol) of 4′-demethylepipodophyllotoxin and 160 mg (1 mmol) of 2-naphthalenethiol were dried under vacuum for 1 h, the mixture was stirred under vacuum for 1-3 h with 15 ml of methanesulfonyl chloride as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(naphthalene-2)-4′-demethylepipodophyllotoxin: the separation and purification were performed using silica gel column chromatography and gel column chromatography in the same manner as in Example 1.

Compound 20 4β-S-(Naphthalen-2)-4′-demethylpodophyllotoxin:white powder, $C_{31}H_{26}O_7S$ $^1$H NMR (400 MHz, CDCl$_3$) δ 7.82-7.73 (m, 4H), 7.58-7.39 (m, 3H), 7.03 (s, 1H), 6.47 (s, 1H), 6.32 (s, 2H), 5.98 (d, J=1.1 Hz, 1H), 5.94 (d, J=1.1 Hz, 1H), 5.45 (s, 1H), 4.96 (d, J=4.3 Hz, 1H), 4.58 (d, J=5.2 Hz, 1H), 4.33-4.12 (m, 2H), 3.77 (s, 6H), 3.40 (dd, J=13.7, 5.2 Hz, 1H), 3.30-3.17 (m, 1H). $^{13}$C NMR (100 MHz, CDCl$_3$) δ 174.57, 152.73, 148.04, 147.25, 146.39, 134.08, 133.70, 133.36, 132.15, 132.10, 131.06, 129.17, 128.53, 127.82, 127.46, 127.11, 127.04, 126.38, 110.12, 109.98, 107.99, 101.54, 69.58, 56.48, 49.67, 43.52, 42.12, 37.94. MS-ESI: 599.52[M+K]$^+$

Example 21 Synthesis and Purification of 4β-S-(1H-imidazo [4,5-B] pyridin-2)-podophyllotoxin (Compound 21)

(1) Synthesis of 4β-S-(1H-imidazo[4,5-B]pyridin-2)-podophyllotoxin: 414 mg (1 mmol) of podophyllotoxin and 151 mg (1 mmol) of 1H-imidazo[4,5-B]pyridine-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(1H-imidazo[4,5-B]pyridin-2)-podophyllotoxin: the separation and purification were performed using silica gel column chromatography and gel column chromatography in the same manner as in Example 1.

Compound 21 4β-S-(1H-imidazo[4,5-B]pyridin-2)-podophyllotoxin:white powder, $C_{28}H_{25}N_3O_7S$ $^1$H NMR (400 MHz, CDCl$_3$) δ 8.23 (s, 1H), 8.08 (d, J=7.9 Hz, 1H), 7.30 (s, 1H), 6.95 (s, 1H), 6.47 (s, 1H), 6.30 (s, 2H), 5.98 (d, J=1.2 Hz, 1H), 5.97 (d, J=1.2 Hz, 1H), 5.73 (d, J=3.9 Hz, 1H), 4.59 (d, J=5.1 Hz, 1H), 4.46-3.85 (m, 2H), 3.80 (s, 3H), 3.75 (s, 6H), 3.44-3.27 (m, 1H), 3.15 (dd, J=13.8, 5.1 Hz, 1H). $^{13}$C NMR (100 MHz, CDCl$_3$) δ 175.08, 159.38, 150.22, 148.57, 147.48, 147.21, 136.45, 134.54, 133.20, 132.44, 130.58, 126.70, 124.62, 117.74, 109.53, 109.47, 108.04, 101.69, 70.57, 55.37, 49.11, 43.31, 42.19, 37.18. MS-ESI: 570.53[M+Na]$^+$

Example 22 Synthesis and Purification of 4β-S-(1H-imidazo[4,5B]pyridin-2)-4′-demethylepipodophyllotoxin (Compound 22)

(1) Synthesis of 4β-S-(1H-imidazo[4,5-B]pyridin-2)-4′-demethylepipodophyllotoxin: 400 mg (1 mmol) of 4′-demethylepipodophyllotoxin and 151 mg (1 mmol) of 1H-imidazo[4,5-B]pyridin-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S -(1H-imidazo[4,5B]pyridin-2)-4′-demethylepipodophyllotoxin: the separation and purification were performed using silica gel column chromatography and gel column chromatography in the same manner as in Example 1.

Compound 22 4β-S-(1H-imidazo[4,5-B]pyridin-2)-4′-demethylepipodophyllotoxin:white powder, $C_{27}H_{23}N_3O_7$ $^1$H NMR (400 MHz, CD$_3$OD) δ 8.37 (d, J=5.6 Hz, 1H), 8.22 (dd, J=8.0, 1.0 Hz, 1H), 7.48 (dd, J=8.0, 5.7 Hz, 1H), 7.02 (s, 1H), 6.47 (s, 1H), 6.34 (s, 2H), 5.99 (d, J=1.2 Hz, 1H), 5.97 (d, J=1.2 Hz, 1H), 5.77 (d, J=4.0 Hz, 1H), 4.60 (d, J=5.2 Hz, 1H), 4.50-3.93 (m, 2H), 3.73 (s, 6H), 3.51-3.35 (m, 1H), 3.33 (dd, J=13.7, 5.2 Hz, 1H). $^{13}$C NMR (100 MHz, CD$_3$OD) δ 175.08, 159.38, 150.22, 148.57, 147.48, 147.21, 136.45, 134.54, 133.20, 132.44, 130.58, 126.70, 124.62, 117.74, 109.53, 109.47, 108.04, 101.69, 70.57, 55.37, 49.11, 43.31, 42.19, 37.18. MS-ESI: 556.41[M+Na]$^+$

Example 23 Synthesis and Purification of 4β-S-(1-phenyltetrazol-5)-podophyllotoxin (Compound 23)

(1) Synthesis of 4β-S-(1-phenyltetrazol-5)-podophyllotoxin: 414 mg (1 mmol) of podophyllotoxin and 178 mg (1 mmol) of 1-phenyltetrazol-5-thiol were dried under vacuum for 1 h, the mixture was stirred under vacuum for 1-3 h with 15 ml of boron trifluoride diethyl ether as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(1-phenyltetrazol-5)-podophyllotoxin: the separation and purification were performed using silica gel column chromatography and gel column chromatography in the same manner as in Example 1.

Compound 23: 4β-S-(1-phenyltetrazol-5)-podophyllotoxin:white powder, $C_{29}H_{26}N_4O_7S$ $^1$H NMR (400 MHz, CDCl$_3$) δ 7.63-7.46 (m, 5H), 6.92 (s, 1H), 6.46 (s, 1H), 6.27 (s, 2H), 5.97 (d, J=1.2 Hz, 1H), 5.94 (d, J=1.1 Hz, 1H), 5.70 (d, J=4.2 Hz, 1H), 4.58 (d, J=5.5 Hz, 1H), 4.57-3.81 (m, 2H), 3.79 (s, 3H), 3.74 (s, 6H), 3.46-3.32 (m, 1H), 3.15 (dd, J=13.8, 5.2 Hz, 1H). $^{13}$C NMR (100 MHz, CDCl$_3$) δ 173.78, 153.41, 152.65, 148.81, 147.62, 137.29, 134.80, 133.23, 132.86, 130.48, 129.99, 126.02, 123.57, 110.05, 108.10, 101.80, 76.72, 70.47, 60.76, 56.18, 51.00, 43.64, 42.43, 36.90. MS-ESI: 575.12[M+H]$^+$

Example 24 Synthesis and Purification of 4β-S-(1-phenyltetrazol-5)-4′-demethylepipodophyllotoxin (Compound 24)

(1) Synthesis of 4β-S-(1-phenyltetrazol-5)-4′-demethylepipodophyllotoxin: 400 mg (1 mmol) of 4′-demethylepipodophyllotoxin and 178 mg (1 mmol) of 1-phenyltetrazol-5-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(1-phenyltetrazol-5)-4'-demethylepipodophyllotoxin: the separation and purification were performed using silica gel column chromatography and gel column chromatography in the same manner as in Example 1.

Compound 24 4β-S-(1-phenyltetrazol-5)-4'-demethylepipodophyllotoxin: white powder, $C_{28}H_{24}N_4O_7S$ $^1$H NMR (400 MHz, CDCl$_3$) δ 7.60-7.50 (m, 5H), 6.92 (s, 1H), 6.46 (s, 1H), 6.27 (s, 2H), 5.99 (d, J=12 Hz, 1H), 5.98 (d, J=1.2 Hz, 1H), 5.69 (d, J=4.2 Hz, 1H), 4.62-4.48 (m, 2H), 3.84-3.79 (m, 1H), 3.77 (s, 6H), 3.43-3.32 (m, 3.13 (dd, J=13.7, 5.2 Hz, 1H). $^{13}$C NMR (100 MHz, CDCl$_3$) δ 173.85, 153.45, 148.79, 147.57, 146.50, 134.21, 133.25, 133.06, 130.47, 130.30, 129.99, 126.04, 123.59, 110.03, 107.80, 101.78, 77.05, 76.73, 70.46, 56.45, 51.01, 43.49, 42.55, 36.84. MS-ESI: 561.41[M+H]$^+$ Example 25 Synthesis and Purification of 4β-S-(3-phenyl-1,3,4-thiadiazol-2(3H)thione potassium salt-5)-podophyllotoxin (Compound 25)

(1) Synthesis of 4β-S-(3-phenyl-1,3,4-thiadiazol-2(3H) thione potassium salt-5)-podophyllotoxin: 414 mg (1 mmol) of podophyllotoxin and 265 mg (1 mmol) of 3-phenyl-1,3,4-thiadiazol-2 (3H) thione potassium salt-5-thiol were dried under vacuum for 1 h, the mixture was stirred under vacuum for 1-3 h with 15 ml of boron trifluoride diethyl ether as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(3-phenyl-1,3,4-thiadiazol-2(3H)thione potassium salt-5)-podophyllotoxin: the separation and purification were performed using silica gel column chromatography and gel column chromatography in the same manner as in Example 1.

Compound 25 4β-S-(3-phenyl-1,3,4-thiadiazol-2(3H) thione potassium salt-5)-podophyllotoxin:white powder, $C_{30}H_{27}KN_2O_7S_3$ $^1$HNMR (400 MHz, CDCl$_3$) δ 7.70-7.64 (m, 2H), 7.55-7.41 (m, 3H), 6.94 (s, 1H), 6.48 (s, 1H), 6.25 (s, 2H), 5.99 (d, J=1.2 Hz, 1H), 5.98 (d, J=1.2 Hz, 1H), 5.32 (d, J=4.1 Hz, 1H), 5.28 (s, 1H), 4.59 (d, J=5.1 Hz, 1H), 4.47-4.03 (m, 2H), 3.78 (s, 3H) 3.73 (s, 6H), 3.31-3.19 (m, 1H), 3.14 (dd, J=13.7, 5.1 Hz, 1H). $^{13}$C NMR (100 MHz, CDCl$_3$) δ 185.55, 173.65, 154.97, 152.63, 148.83, 147.69, 138.15, 137.38, 134.85, 132.92, 129.45, 129.24, 125.81, 125.73, 110.12, 109.97, 108.25, 101.84, 70.27, 60.73, 5630, 50.22, 43.55, 42.45, 36.94. MS-ESI: 681.13[M+H]$^+$ Example 26 Synthesis and Purification of 4β-S-(3-phenyl-1,3,4-thiadiazol-2(3H)thione potassium salt-5)-4'-demethylepipodophyllotoxin (Compound 26)

(1) Synthesis of 4β-S-(3-phenyl-1,3,4-thiadiazol-2(3H) thione potassium salt-5)-4'-demethylepipodophyllotoxin: 400 mg (1 mmol) of 4'-demethylepipodophyllotoxin and 265 mg (1 mmol) of 3-phenyl-1,3,4-thiadiazol-2(3H)thione potassium salt-5-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(3-phenyl-1,3,4-thiadiazol-2(3H)thione potassium salt-5)-4'-demethylepipodophyllotoxin: the separation and purification were performed using silica gel column chromatography and gel column chromatography in the same manner as in Example 1.

Compound 26 4β-S-(3-phenyl-1,3,4-thiadiazol-2(3H) thione potassium salt-5)-4'-demethylepipodophyllotoxin: white powder, $C_{29}H_{25}KN_2O_7S_3$ $^1$H NMR (400 MHz, CDCl$_3$) δ 7.72-7.64 (m, 2H), 7.55-7.41 (m, 3H), 6.93 (s, 1H), 6.47 (s, 1H), 6.26 (s, 2H), 5.99 (d, J=1.2 Hz, 1H), 5.98 (d, J=1.2 Hz, 1H), 5.44 (s, 1H), 5.32 (d, J=4.1 Hz, 1H), 5.29 (s, 1H), 4.59 (d, J=5.1 Hz, 1H), 4.47-4.03 (m, 2H), 3.76 (s, 6H), 3.29-3.19 (m, 1H), 3.12 (dd, J=13.7, 5.1 Hz, 1H). $^{13}$CNMR (100 MHz, CDCl$_3$) δ 185.57, 173.72, 155.00, 148.82, 147.64, 146.45, 138.16, 134.25, 133.10, 130.34, 129.46, 129.25, 125.77, 110.13, 109.91, 107.91, 101.82, 70.25, 56.51, 50.24, 43.39, 42.55, 36.88. MS-ESI: 667.01[M+H]$^+$ Example 27 Synthesis and Purification of 4β-S-(4-(4-pyridyl)thiazol-2)-podophyllotoxin (Compound 27)

(1) Synthesis of 4β-S-(4-(4-pyridyl)thiazol-2)-podophyllotoxin: 414 mg (1 mmol) of podophyllotoxin and 194 mg (1 mmol) of 4-(4-pyridyl)thiazol-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(4-(4-pyridyl) thiazol-2)-podophyllotoxin: the separation and purification were performed using silica gel column chromatography and gel column chromatography in the same manner as in Example 1.

Compound 27 4β-S-(4-(4-pyridyl)thiazol-2)-podophyllotoxin:white powder, $C_{30}H_{28}N_2O_7S_2$ $^1$H NMR (400 MHz, CDCl$_3$) δ 8.64 (d, J=5.9 Hz, 2H), 7.72 (d, J=1.6 Hz, 1H), 7.71 (d, J=1.5 Hz, 1H), 7.64 (s, 1H), 6.99 (s, 1H), 6.48 (s, 1H), 6.32 (s, 2H), 5.97 (d, J=1.2 Hz, 1H), 5.95 (d, J=1.2 Hz, 1H), 5.57 (d, J=4.2 Hz, 1H), 4.61 (d, J=5.2 Hz, 1H), 4.48-4.04 (m, 2H), 3.79 (s, 3H), 3.76 (s, 6H), 3.41-3.31 (m, 1H), 3.22 (dd, J=13.7, 5.2 Hz, 1H). $^{13}$C NMR (100 MHz, CDCl$_3$) δ 174.24, 164.72, 152.59, 152.36, 150.47, 148.45, 147.49, 140.44, 137.32, 135.28, 132.56, 127.00, 120.27, 116.41, 110.13, 110.00, 108.38, 101.68, 70.69, 60.75, 56.33, 50.63, 43.67, 42.45, 37.26, MS-ESI: 593.13[M+H]$^+$ Example 28 Synthesis and Purification of 4β-S-(4-(4-pyridyl) thiazol-2)-4'-demethylepipodophyllotoxin (Compound 28)

(1) Synthesis of 4β-S-(4-(4-pyridyl)thiazol-2)-4'-demethylepipodophyllotoxin: 400 mg (1 mmol) of 4'-demethylepipodophyllotoxin and 194 mg (1 mmol) of 4-(4-pyridyl) thiazol-2-thiol were dried under vacuum for 1 h, the mixture was stirred under vacuum for 1-3 h with 15 ml of trifluoroacetic acid as a solvent in an ice bath, and the reaction end point was detected with chloroform acetone as a developing solvent. The reaction system was added into 20-50 times of volume of deionized water and filtered; a filter cake was collected, washed and dried to obtain a crude product.

(2) Separation and purification of 4β-S-(4-(4-pyridyl) thiazol-2)-4'-demethylepipodophyllotoxin: the separation and purification were performed using silica gel column chromatography and gel column chromatography in the same manner as in Example 1.

Compound 28 4β-S-(4-(4-pyridyl)thiazol-2)-4′-demethylepipodophyllotoxin:white powder, $C_{29}H_{26}N_2O_7S_2$, $^1$H NMR (400 MHz, CDCl$_3$) δ 8.64 (d J=5.9 Hz, 2H), 7.72 (d, J=1.6 Hz, 1H), 7.71 (d, J=1.5 Hz, 1H), 7.64 (s, 1H), 6.99 (s, 1H), 6.48 (s, 1H), 6.32 (s, 2H), 5.97 (d, J=1.2 Hz, 1H), 5.95 (d, J=1.2 Hz, 1H), 5.72 (s, 1H), 5.57 (d, J=4.2 Hz, 1H), 4.61 (d, J=5.2 Hz, 1H), 4.47-4.04 (m, 2H), 3.79 (s, 6H), 3.42-3.30 (m, 1H), 3.21 (dd, J=13.7, 5.1 Hz, 1H). 13C NMR (100 MHz, CDCl$_3$) δ 174.31, 164.76, 152.40, 150.50, 148.44, 147.44, 146.51, 140.42, 134.30, 132.78, 130.69, 127.02, 120.27, 116.33, 110.05, 108.06, 101.66, 70.68, 56.55, 50.66, 43.51, 42.58, 37.18. MS-ESI: 579.24[M+H]$^+$ Test Example 1 Activity Test of the Compound Prepared in the Example of the Present Invention for Inhibiting Tumor Cells I. Test Materials Test compounds: Compounds prepared in Examples 1-28, numbered Compounds 1-28, respectively;

A control compound: podophyllotoxin and 4′-demethylepipodophyllotoxin were purchased from Xi′an Helin Bioengineering Co., Ltd., purity 98%; etoposide;

A cell strain: HepG2, HeLa cell lines and human normal hepatocytes HL-7702 were purchased from Wuhan Boster Biological Technology Co., Ltd;

II. Test Methods

HepG2, HeLa cell lines and human normal liver cells HL-7702 in a logarithmic growth period were centrifuged at 1000 rpm for 5 min, and the supernatant was discarded, the cells were suspended with a suitable amount of culture medium to adjust the cell concentration to 3.5×10$^4$/well, the cells were seeded in 96-well plates, and the following experimental groups were set:

One negative control group; 28 test groups of the same concentration (i. e: Compound 1-28 groups); three control groups: podophyllotoxin group, 4′-demethylepipodophyllotoxin group and etoposide group.

0.10 mL of cells were added to each well and incubated at 37° C., 5% CO$_2$ and saturated humidity for 24 h by using 10% calf serum-containing RPMI1640 as a culture medium, the culture medium was discarded when the cell density was nearly 100%; 0.10 M 10% calf serum-containing RPMI1640 culture medium with the same amount of compounds 1-28 was added to 28 test groups respectively; 0.10 M 10% calf serum-containing RPMI1640 culture medium with podophyllotoxin, 4′-demethylepipodophyllotoxin or etoposide was added into the podophyllotoxin group, 4′-demethylepipodophyllotoxin group and etoposide group respectively; the dosage of podophyllotoxin, 4′-demethylepipodophyllotoxin or etoposide was completely the same as the dosage of the compounds 1-28; the negative control group was treated with the culture medium with a final concentration of 0.5% DMSO, and each group was treated with 3 duplicate wells and cultured for 48 h; 10 μl of 5 mg/ml MTT was added per well, standing for 4 h at 37° C. 100 μl of DMSO was added to each well, followed by shaking on a shaker for 30 min at 37° C., the absorbance (OD) was measured at 492 nm, and the MTT ratio was calculated as the OD value of drug group/OD value of negative control group.

III. Test Results

The test results are shown in Table 1. As can be seen from Table 1, the antitumor activities of the compounds 1-28 on HepG2, HeLa and HL-7702 cell lines are obviously improved compared with that of podophyllotoxin, 4′-demethylepipodophyllotoxin and podophyllotoxin derivative etoposide which is currently marketed as an antitumor drug; the toxicities of compound 8-10 on HL-7702 cell line was significantly lower than that of podophyllotoxin, 4′-demethylepipodophyllotoxin and etoposide.

TABLE 1

IC$_{50}$ values of 4-sulfur substituted podophyllotoxin derivatives against in vitro tumor strains and normal cell lines

| Compounds | IC$_{50}$ (μM) | | |
|---|---|---|---|
| | HepG2 | HeLa | HL-7702 |
| 1 | 2.04 ± 0.30 | 1.86 ± 0.20 | 57.02 ± 1.10 |
| 2 | 4.50 ± 0.45 | 4.58 ± 0.13 | 42.32 ± 1.52 |
| 3 | 5.05 ± 0.78 | 10.09 ± 0.22 | 69.79 ± 1.23 |
| 4 | 7.37 ± 0.32 | 39.36 ± 0.35 | 54.88 ± 0.98 |
| 5 | 2.28 ± 0.10 | 9.50 ± 0.43 | 44.51 ± 1.00 |
| 6 | 4.24 ± 0.97 | 55.28 ± 0.21 | 50.96 ± 0.88 |
| 7 | 1.00 ± 0.06 | 1.47 ± 0.32 | 97.01 ± 2.10 |
| 8 | 1.49 ± 0.12 | 2.30 ± 0.12 | 966.25 ± 7.31 |
| 9 | 0.89 ± 0.07 | 1.25 ± 0.31 | >1000 |
| 10 | 1.55 ± 0.29 | 1.49 ± 0.14 | 2000.29 ± 12.80 |
| 11 | 5.25 ± 0.13 | >100 | 70.73 ± 1.65 |
| 12 | 10.22 ± 0.46 | >100 | 56.78 ± 1.32 |
| 13 | 7.31 ± 0.40 | 9.31 ± 0.60 | 60.06 ± 1.60 |
| 14 | 7.94 ± 0.21 | 11.94 ± 0.99 | 78.66 ± 2.50 |
| 15 | 5.23 ± 0.35 | 7.23 ± 0.44 | 43.26 ± 3.50 |
| 16 | 22.27 ± 1.46 | 32.27 ± 1.87 | 68.32 ± 4.50 |
| 17 | 0.92 ± 0.05 | 1.15 ± 0.16 | 8.15 ± 0.87 |
| 18 | 2.09 ± 0.17 | 7.60 ± 0.51 | 11.34 ± 1.87 |
| 19 | 3.06 ± 0.11 | 3.91 ± 0.42 | 90.91 ± 3.49 |
| 20 | 6.02 ± 0.25 | 5.54 ± 0.30 | 76.77 ± 2.11 |
| 21 | 4.23 ± 0.36 | 64.23 ± 0.45 | 56.57 ± 2.34 |
| 22 | 8.31 ± 0.43 | >100 | 33.47 ± 3.25 |
| 23 | 6.17 ± 0.27 | 15.85 ± 0.56 | 87.11 ± 4.20 |
| 24 | 59.69 ± 0.31 | 9.73 ± 0.11 | 70.99 ± 3.67 |
| 25 | 2.20 ± 0.28 | 31.91 ± 0.42 | 57.51 ± 2.99 |
| 26 | 5.70 ± 0.33 | 48.49 ± 0.38 | 43.42 ± 4.00 |
| 27 | 0.89 ± 0.19 | 1.95 ± 0.36 | 71.41 ± 2.71 |
| 28 | 29.23 ± 1.34 | 24.14 ± 1.29 | 60.13 ± 2.88 |

TABLE 1-continued

IC$_{50}$ values of 4-sulfur substituted podophyllotoxin derivatives against in vitro tumor strains and normal cell lines

| Compounds | IC$_{50}$ (μM) | | |
|---|---|---|---|
| | HepG2 | HeLa | HL-7702 |
| Podophyllotoxin | 55.53 ± 0.24 | 75.81 ± 0.73 | 67.18 ± 0.24 |
| 4-Demethylepipodophyllotoxin | 49.32 ± 0.38 | 63.09 ± 0.49 | 52.88 ± 0.85 |
| Etoposide | 20.72 ± 1.7 | 25.40 ± 2.9 | 28.75 ± 3.4 |

After activity evaluation, two low-toxicity compounds of 8 and 10 were screened out, and added with new normal cell lines including human cervical immortalized cells H8, human embryonic lung cells MRC-5 and human mammary epithelial cells HMEC and corresponding tumor cells including human lung cancer cell A549 and breast cancer cell MCF7 for further studying on toxicities and activities of the compounds.

As can be seen from Table 2, the antitumor activities of compounds 8 and 10 on A549 and MCF7 cell lines were significantly improved than that of etoposide, and the toxicities on normal cell lines H8, MRC-5 and HMEC were significantly lower than that of etoposide.

TABLE 2

IC$_{50}$ values for compounds 8 and 10 against in vitro tumor strains and normal cell lines.

| Compounds | IC$_{50}$ (μM) | | | | |
|---|---|---|---|---|---|
| | H8 | A549 | MRC-5 | MCF7 | HMEC |
| 8 | 528.73 ± 1.89 | 3.25 ± 0.22 | 425.56 ± 2.13 | 1.25 ± 0.17 | 250.32 ± 1.45 |
| 10 | 518.90 ± 1.90 | 2.34 ± 0.16 | 348.91 ± 3.10 | L4 ± 0.10 | 323.45 ± 3.21 |
| Etoposide | 80.12 ± 1.35 | 20.12 ± 1.95 | 30.34 ± 1.21 | 56.81 ± 1.22 | 23.23 ± 1.34 |

The invention claimed is:

1. A compound of formula (V) or a pharmaceutically acceptable salt thereof:

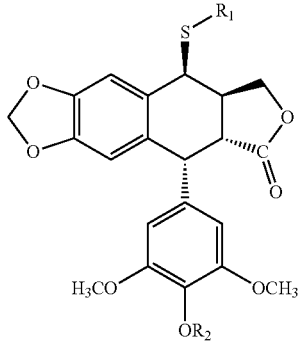

formula (V)

wherein R$_1$ is

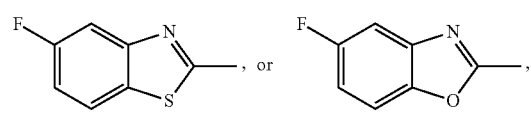

and
R$_2$ is hydrogen or —CH$_3$.

2. A method for preparing the compound of claim 1, the method comprising the steps of:
introducing a reaction monomer into position-4 of the C ring in podophyllotoxin or 4'-demethylepipodophyllotoxin through a nucleophilic substitution reaction to obtain a reaction solution, wherein the reaction monomer is 5-fluorobenzothiazol-2-thiol, or 5-fluorobenzoxazol-2-thiol.

3. The method of claim 2, wherein the nucleophilic substitution reaction is performed under the following conditions: dissolving the podophyllotoxin or the 4'-demethylepipodophyllotoxin in an organic solvent, adding the reaction monomer followed by stirring, wherein the organic solvent is trifluoroacetic acid, methanesulfonyl chloride or boron trifluoride diethyl ether.

4. The method of claim 3, wherein a molar ratio of the podophyllotoxin or the 4'-demethylepipodophyllotoxin to the reaction monomer is 1:1-10.

5. The method of claim 3, wherein the nucleophilic substitution reaction is performed at −20-40° C.

6. The method of claim 5, wherein the nucleophilic substitution reaction is performed at −10-10° C.

7. The method of claim 5, wherein the nucleophilic substitution reaction is performed at 0-10° C.

8. The method of claim 3, further comprising the steps of: pouring the reaction solution after the nucleophilic substitution reaction into deionized water, followed by separating out and filtering to obtain a filer cake, and drying the filter cake to obtain a crude product of the compound, wherein a volume of the deionized water is 20-50 times that of the reaction solution after the nucleophilic substitution reaction.

9. The method of claim 8, further comprising the steps of: sequentially separating the crude products by using silica gel column chromatography and gel column chromatography to obtain the compound in a purified form.

10. The method of claim 3, wherein a molar ratio of the podophyllotoxin or the 4'-demethylepipodophyllotoxin to the reaction monomer is 1:1-8.

11. The method of claim 3, wherein a molar ratio of the podophyllotoxin or the 4'-demethylepipodophyllotoxin to the reaction monomer is 1:1.

12. The method of claim 3, wherein the nucleophilic substitution reaction is performed at −20-20° C.

13. A method of antitumor treatment, the method comprising administering an effective amount of the compound or the salt thereof of claim 1.

14. An antitumor pharmaceutical composition comprising an effective amount of the compound or the salt thereof of claim 1 and a pharmaceutically acceptable carrier.

* * * * *